(12) United States Patent
Markau et al.

(10) Patent No.: US 6,794,177 B2
(45) Date of Patent: Sep. 21, 2004

(54) MODIFIED DNA-POLYMERASE FROM CARBOXYDOTHERMUS HYDROGENOFORMANS AND ITS USE FOR COUPLED REVERSE TRANSCRIPTION AND POLYMERASE CHAIN REACTION

(75) Inventors: Ursula Markau, Polling (DE);
Christine Ebenbichler, Antdorf (DE);
Gunthar Achhammer, Penzberg (DE);
Waltraud Ankenbauer, Penzberg (DE)

(73) Assignee: Roche Diagnostics GmbH, Mannheim (DE)

( * ) Notice: Subject to any disclaimer, the term of this patent is extended or adjusted under 35 U.S.C. 154(b) by 68 days.

(21) Appl. No.: 10/072,436

(22) Filed: Feb. 5, 2002

(65) Prior Publication Data

US 2002/0160399 A1 Oct. 31, 2002

Related U.S. Application Data

(63) Continuation of application No. 09/204,208, filed on Dec. 1, 1998.

(30) Foreign Application Priority Data

Dec. 2, 1997 (EP) ............................................. 97121151

(51) Int. Cl.⁷ ............................. C12N 1/20; C12N 9/12; C12N 15/00
(52) U.S. Cl. .................... 435/252.3; 435/194; 435/183; 435/320.1; 536/23.1; 536/23.2; 536/23.7; 536/23.5; 530/350
(58) Field of Search ............................. 435/23.7, 194, 435/183, 320.1, 252.3; 530/350; 536/23.5, 23.1, 23.2

(56) References Cited

U.S. PATENT DOCUMENTS

| | | | |
|---|---|---|---|
| 5,436,326 A | 7/1995 | Ishino et al. ................ | 536/23.2 |
| 5,474,920 A | 12/1995 | Moses ......................... | 435/194 |
| 5,616,494 A | 4/1997 | Barnes ..................... | 435/252.3 |
| 5,674,738 A | 10/1997 | Abramson et al. ........ | 435/252.3 |
| 5,693,517 A | 12/1997 | Gelfand et al. ............. | 435/193 |
| 5,814,506 A | 9/1998 | Kong et al. ................. | 935/194 |
| 5,830,714 A | 11/1998 | Swaminathan et al. .... | 435/91.2 |

FOREIGN PATENT DOCUMENTS

| | | |
|---|---|---|
| EP | 0 699 760 | 3/1996 |
| EP | 0 757 100 | 2/1997 |
| EP | 0 776 970 | 6/1997 |
| EP | 0 810 288 | 12/1997 |
| WO | WO 92/03556 | 3/1992 |
| WO | WO 92/06200 | 4/1992 |
| WO | WO 96/10640 | 4/1996 |
| WO | WO 96/14417 | 5/1996 |
| WO | WO 97/21821 | 6/1997 |
| WO | WO 97/39113 | 10/1997 |

OTHER PUBLICATIONS

Chiocchia, G, et al., "Highly Sensitive Method to Detect mRNAs in Individual Cells by Direct RT–PCR Using Tth DNA Polymerase", *BioTechniques,* 22, pp. 312–318 (1997).

Daniel, E.S., et al., "Method to Identify Biases in PCR Amplification of T–Cell Receptor Variable Regions Genes", *BioTechniques,* 20, pp. 600–602 (1996).

Freeman, W.M., et al., "Use of Elevated Reverse Transcription Reaction Temperatures in RT–PCR", *BioTechniques,* 20, pp. 782–783 (1996).

Juhasz, A., et al., "Sensitivity of Tyrosinase mRNA Detection by RT–PCR: rTth DNA Polymerase vs. MMLV–RT and AmpliTaq® Polymerase", *BioTechniques,* 20, pp. 592–600 (1996).

*Primary Examiner*—Richard Hutson
(74) *Attorney, Agent, or Firm*—Pennie & Edmonds

(57) ABSTRACT

A purified DNA polymerase exhibiting reverse transcriptase activity in the presence of magnesium ions and/or manganese ions having reduced or no 5'-3'-exonuclease activity and substantially no RNaseH activity and obtainable from *Carboxydothermus hydrogenoformans*.

9 Claims, 7 Drawing Sheets

Figure 1A

Nucleic acid (SEQ ID NO: 10) and protein (SEQ ID NO: 11) sequence of Δ Chy DNA polymerase

```
1    ATGGAAAAGCTTGCCGAACACGAAAATTTAGCAAAAATATCGAAACAATTAGCTACAATC
1      M  E  K  L  A  E  H  E  N  L  A  K  I  S  K  Q  L  A  T  I

61   CTGCGGGAAATACCGTTAGAAATCTCCCTGGAAGATTTAAAAGTTAAAGAACCTAATTAT
21     L  R  E  I  P  L  E  I  S  L  E  D  L  K  V  K  E  P  N  Y

121  GAAGAAGTTGCTAAATTATTTCTTCACCTTGAGTTTAAAAGCTTTTTAAAAGAAATAGAA
41     E  E  V  A  K  L  F  L  H  L  E  F  K  S  F  L  K  E  I  E

181  CCAAAAATAAAGAAAGAATACCAGGAAGGTAAAGATTTGGTGCAAGTTGAAACTGTAGAA
61     P  K  I  K  K  E  Y  Q  E  G  K  D  L  V  Q  V  E  T  V  E

241  ACGGAAGGACAGATTGCAGTAGTTTTTAGTGATGGATTTTATGTTGATGACGGGGAAAAA
81     T  E  G  Q  I  A  V  V  F  S  D  G  F  Y  V  D  D  G  E  K

301  ACAAAGTTTTACTCTTTAGACCGGCTGAATGAAATAGAGGAAATATTTAGGAATAAAAAA
101    T  K  F  Y  S  L  D  R  L  N  E  I  E  E  I  F  R  N  K  K

361  ATTATTACCGACGATGCCAAAGGAATTTATCATGTCTGTTTAGAAAAAGGTCTGACTTTT
121    I  I  T  D  D  A  K  G  I  Y  H  V  C  L  E  K  G  L  T  F

421  CCCGAAGTTTGTTTTGATGCGCGGATTGCAGCTTATGTTTTAAACCCGGCCGACCAAAAT
141    P  E  V  C  F  D  A  R  I  A  A  Y  V  L  N  P  A  D  Q  N

481  CCCGGCCTCAAGGGGCTTTATCTAAAGTATGACTTACCGGTGTATGAAGATGTATCTTTA
161    P  G  L  K  G  L  Y  L  K  Y  D  L  P  V  Y  E  D  V  S  L

541  AACATTAGAGGGTTGTTTTATTTAAAAAAAGAAATGATGAGAAAAATCTTTGAGCAGGAG
181    N  I  R  G  L  F  Y  L  K  K  E  M  M  R  K  I  F  E  Q  E

601  CAAGAAAGGTTATTTTATGAAATAGAACTTCCTTTAACTCCAGTTCTTGCTCAAATGGAG
201    Q  E  R  L  F  Y  E  I  E  L  P  L  T  P  V  L  A  Q  M  E

661  CATACCGGCATTCAGGTTGACCGGGAAGCTTTAAAAGAGATGTCGTTAGAGCTGGGAGAG
221    H  T  G  I  Q  V  D  R  E  A  L  K  E  M  S  L  E  L  G  E
```

Figure 1B

```
 721   CAAATTGAAGAGTTAATCCGGGAAATTTATGTGCTGGCGGGGGAAGAGTTTAACTTAAAC
 241    Q   I   E   E   L   I   R   E   I   Y   V   L   A   G   E   E   F   N   L   N

781   TCGCCCAGGCAGCTGGGAGTTATTCTTTTTGAAAAACTTGGGCTGCCGGTAATTAAAAAG
 261    S   P   R   Q   L   G   V   I   L   F   E   K   L   G   L   P   V   I   K   K

841   ACCAAAACGGGCTACTCTACCGATGCGGAGGTTTTGGAAGAGCTCTTGCCTTTCCACGAA
 281    T   K   T   G   Y   S   T   D   A   E   V   L   E   E   L   L   P   F   H   E

901   ATTATCGGCAAAATATTGAATTACCGGCAGCTTATGAAGTTAAAATCCACTTATACTGAC
 301    I   I   G   K   I   L   N   Y   R   Q   L   M   K   L   K   S   T   Y   T   D

961   GGCTTAATGCCTTTAATAAATGAGCGTACCGGTAAACTTCACACTACTTTTAACCAGACC
 321    G   L   M   P   L   I   N   E   R   T   G   K   L   H   T   T   F   N   Q   T

1021   GGTACTTTAACCGGACGCCTGGCGTCTTCGGAGCCCAATCTCCAAAATATTCCCATCCGG
 341    G   T   L   T   G   R   L   A   S   S   E   P   N   L   Q   N   I   P   I   R

1081   TTGGAACTCGGTCGGAAATTACGCAAGATGTTTATACCTTCACCGGGGTATGATTATATT
 361    L   E   L   G   R   K   L   R   K   M   F   I   P   S   P   G   Y   D   Y   I

1141   GTTTCGGCGGATTATTCCCAGATTGAATTAAGGCTTCTTGCCCATTTTTCCGAAGAGCCC
 381    V   S   A   D   Y   S   Q   I   E   L   R   L   L   A   H   F   S   E   E   P

1201   AAGCTTATTGAAGCTTACCAAAAAGGGGAGGATATTCACCGGAAAACGGCCTCCGAGGTG
 401    K   L   I   E   A   Y   Q   K   G   E   D   I   H   R   K   T   A   S   E   V

1261   TTCGGTGTATCTTTGGAAGAAGTTACTCCCGAGATGCGCGCTCATGCCAAGTCGGTGAAC
 421    F   G   V   S   L   E   E   V   T   P   E   M   R   A   H   A   K   S   V   N

1321   TTCGGCATTGTTTATGGCATTAGTGATTTTGGTTTAGGCAGAGACTTAAAGATTCCCCGG
 441    F   G   I   V   Y   G   I   S   D   F   G   L   G   R   D   L   K   I   P   R

1381   GAGGTTGCCGGTAAGTACATTAAAAATTATTTTGCCAACTATCCCAAAGTGCGGGAGTAT
 461    E   V   A   G   K   Y   I   K   N   Y   F   A   N   Y   P   K   V   R   E   Y
```

Figure 1C

```
1441  CTCGATGAACTTGTCCGTACGGCAAGAGAAAAGGGATATGTGACCACTTTATTTGGGCGA
481    L   D   E   L   V   R   T   A   R   E   K   G   Y   V   T   T   L   F   G   R

1501  AGACGCTATATTCCTGAGCTATCTTCAAAAAACCGCACGGTTCAGGGTTTTGGCGAAAGG
501    R   R   Y   I   P   E   L   S   S   K   N   R   T   V   Q   G   F   G   E   R

1561  ACGGCCATGAATACTCCCCTTCAGGGCTCGGCTGCCGATATTATTAAGCTTGCAATGATT
521    T   A   M   N   T   P   L   Q   G   S   A   A   D   I   I   K   L   A   M   I

1621  AATGTAGAAAAAGAACTTAAAGCCCGTAAGCTTAAGTCCCGGCTCCTTCTTTCGGTGCAC
541    N   V   E   K   E   L   K   A   R   K   L   K   S   R   L   L   L   S   V   H

1681  GATGAGTTAGTTTTAGAAGTGCCGGCGGAAGAGCTGGAAGAGGTAAAAGCGCTGGTAAAA
561    D   E   L   V   L   E   V   P   A   E   E   L   E   E   V   K   A   L   V   K

1741  GGGGTTATGGAGTCGGTGGTTGAACTGAAAGTGCCTTTAATCGCTGAAGTTGGTGCAGGC
581    G   V   M   E   S   V   V   E   L   K   V   P   L   I   A   E   V   G   A   G

1801  AAAAACTGGTATGAAGCGAAGTAA
601    K   N   W   Y   E   A   K   *
```

MODIFIED DNA-POLYMERASE FROM CARBOXYDOTHERMUS HYDROGENOFORMANS AND ITS USE FOR COUPLED REVERSE TRANSCRIPTION AND POLYMERASE CHAIN REACTION

This is a continuation of application Ser. No. 09/204,208, filed Dec. 1, 1998, the content of which is hereby incorporated by reference in its entirety.

This application claims priority to European patent application No. 97.121151.1, filed Dec. 2, 1997.

BACKGROUND OF THE INVENTION

1. Field of the Invention

The present invention relates to a modified DNA-polymerase having reverse transcriptase activity and reduced 5'-3' exonuclease activity derived from a native polymerase which is obtainable from *Carboxydothermus hydrogenoformans*. Furthermore the invention relates to the field of molecular biology and provides methods for amplifying a DNA segment from an RNA template using an enzyme with reverse transcriptase activity (RT-PCR). In another aspect, the invention provides a kit for Coupled High Temperature Reverse Transcription and Polymerase Chain Reaction.

2. Description of Related Art

Heat stable DNA polymerases (EC 2.7.7.7. DNA nucleotidyltransferase, DNA-directed) have been isolated from numerous thermophilic organisms (for example: Kaledin et al. (1980), *Biokhimiya* 45, 644–651; Kaledin et al. (1981) *Biokhimiya* 46, 1576–1584; Kaledin et al. (1982) *Biokhimiya* 47, 1785–1791; Ruttimann et al. (1985) *Eur. J. Biochem.* 149, 41–46; Neuner et al. (1990) *Arch. Microbiol.* 153, 205–207). For some organisms, the polymerase gene has been cloned and expressed (Lawyer et al. (1989) *J. Biol. Chem.* 264, 6427–6437; Engelke et al. (1990) *Anal. Biochem.* 191, 396–400; Lundberg et al. (1991) *Gene* 108, 1–6; Perler et al. (1992) *Proc. Natl. Acad. Sci. USA* 89, 5577–5581).

Thermophilic DNA polymerases are increasingly becoming important tools for use in molecular biology and there is growing interest in finding new polymerases which have more suitable properties and activities for use in diagnostic detection of RNA and DNA, gene cloning and DNA sequencing. At present, the thermophilic DNA polymerases mostly used for these purposes are from Thermus species like Taq polymerase from *T. aquaticus* (Brock et al. (1969) *J. Bacteriol.* 98, 289–297).

The term "reverse transcriptase" describes a class of polymerases characterized as RNA-dependent DNA-polymerases. All known reverse transcriptases require a primer to synthesize a DNA-transcript from an RNA template. Historically, reverse transcriptase has been used primarily to transcribe mRNA into cDNA which can then be cloned into a vector for further manipulation.

Reverse transcription is commonly performed with viral reverse transcriptases like the enzymes isolated from Avian myeloblastosis virus or Moloney murine leukemia virus. Both enzymes mentioned are active in the presence of magnesium ions but have the disadvantages to possess RNase H-activity, which destroys the template RNA during the reverse transcription reaction and have a temperature optimum at 42° C. or 37° C., respectively. Avian myeloblastosis virus (AMV) reverse transcriptase was the first widely used RNA-dependent DNA-polymerase (Verma (1977) *Biochem. Biophys. Acta* 473, 1). The enzyme has 5'-3' RNA-directed DNA polymerase activity, 5'-3' DNA directed DNA polymerase activity, and RNaseH activity. RNaseH is a processive 5'-3' ribonuclease specific for the RNA strand of RNA-DNA hybrids (Perbal (1984), A Practical Guide to Molecular Cloning, Wiley & Sons New York). Errors in transcription cannot be corrected because known viral reverse transcriptases lack the 3'-5' exonuclease activity necessary for proofreading (Saunders and Saunders (1987) Microbial Genetics Applied to Biotechnology, Croom Helm, London). A detailed study of the activity of AMV reverse transcriptase and its associated RNaseH activity has been presented by Berger et al., (1983) *Biochemistry* 22, 2365–2372.

DNA polymerases isolated from mesophilic microorganisms such as *E. coli* have been extensively characterized (see, for example, Bessmann et al. (1957) *J. Biol. Chem.* 233, 171–177 and Buttin and Kornberg (1966) *J. Biol. Chem.* 241, 5419–5427). *E. coli* DNA polymerase I (Pol I) is useful for a number of applications including: nick-translation reactions, DNA sequencing, in vitro mutagenesis, second strand cDNA synthesis, polymerase chain reactions (PCR), and blunt end formation for linker ligation (Maniatis et al., (1982) Molecular Cloning: A Laboratory Manual Cold Spring Harbor, N.Y.).

Several laboratories have shown that some polymerases are capable of in vitro reverse transcription of RNA (Karkas (1973) *Proc. Nat. Acad. Sci. USA* 70, 3834–3838; Gulati et al. (1974) *Proc. Nat. Acad. Sci USA* 71, 1035–1039; and Wittig and Wittig, (1978) *Nuc. Acids Res.* 5, 1165–1178). Gulati et al. found that *E. coli* Pol I could be used to transcribe Qβ viral RNA using oligo(dT)$_{10}$ as a primer. Wittig and Wittig have shown that *E. coli* Pol I can be used to reverse transcribe tRNA that has been enzymatically elongated with oligo(dA). However, as Gulati et al. demonstrated, the amount of enzyme required and the small size of cDNA product suggest that the reverse transcriptase activity of *E. coli* Pol I has little practical value.

Alternative methods are described using the reverse transcriptase activity of DNA polymerases of thermophilic organisms which are active at higher temperatures. Reverse transcription at higher temperatures is of advantage to overcome secondary structures of the RNA template which could result in premature termination of products. Thermostable DNA polymerases with reverse transcriptase activities are commonly isolated from Thermus species. These DNA polymerases however, show reverse transcriptase activity only in the presence of manganese ions. These reaction conditions are suboptimal, because in the presence of manganese ions the polymerase copies the template RNA with low fidelity.

Another feature of the commonly used reverse transcriptases is that they do not contain 3'-5' exonuclease activity. Therefore, misincorporated nucleotides cannot be removed and thus the cDNA copies from the template RNA may contain a significant degree of mutations.

One of the known DNA polymerases having high reverse transcriptase activity is obtainable from *Thermus thermophilus* (Tth polymerase) (WO 91/09944). Tth polymerase, as well as Taq polymerase, lacks 3' to 5' exonucleolytic proofreading activity. This 3' to 5' exonuclease activity is generally considered to be desirable because it allows removal of misincorporated or unmatched bases in the newly synthesized nucleic acid sequences. Another thermophilic pol I-type DNA polymerase isolated from *Thermotoga maritima* (Tma pol) has 3' to 5' exonuclease activity. U.S. Pat. No. 5,624,833 provides means for isolating and producing Tma polymerase. However, both DNA polymerases, Tth as well as Tma polymerase, show reverse transcriptase activity only in the presence of manganese ions.

The DNA polymerase of *Carboxydothermus hydrogenoformans* shows reverse transcription activity in the presence of magnesium ions and in the substantial absence of manganese ions and can be used to reverse transcribe RNA, to detect and amplify (in combination with a thermostable DNA polymerase like Taq) specific sequences of RNA. Using DNA polymerase of *Carboxydothermus hydrogenoformans* polymerase a high specificity of transcription is observed with short incubation times. A high specificity is observed using e.g. 5 min of incubation time and 33 units of DNA polymerase protein. With longer incubation times also with lower amounts of *Carboxydothermus hydrogenoformans* polymerase specific products can be obtained. However an unspecific smear of products is occurring. These unspecific products might be caused by the 5'-3' exonuclease activity of the polymerase which enables the enzyme to cleave the template at secondary structures ("RNaseH"-activity) and to create additional primers which can be elongated by the DNA polymerase activity. The thermostable DNA polymerase from *Carboxydothermus hydrogenoformans* has been identified and cloned and is described in the copending European application with the Application No. 96115873.0, filed Oct. 3, 1996, and incorporated herein by reference.

In summary, reverse transcriptases as MoMULV-RT or AMV-RT perform reverse transcription in the presence of magnesium-ions. However, these enzymes act at temperatures between 37° C. and 55° C. Reverse transcription at higher temperatures would be desirable because secondary structures can be overcome in the template in order to avoid premature termination of the reaction and to assure the production of cDNA without deletions. Other enzymes e.g. DNA polymerase obtainable from Thermus spec. act as reverse transcriptase at temperatures up to 70° C. in the presence of manganese ions. These reaction conditions are suboptimal, because in the presence of manganese ions the polymerase copies the template RNA with low fidelity and the RNA strand will be degraded. Degradation of the RNA strand occurs faster in the presence of manganese ions as in the presence of magnesium ions. Therefore, if manganese ions are present complexation of the manganese ions (e.g. with EDTA) is required after cDNA synthesis in order to obtain a higher fidelity during cDNA amplification in the subsequent PCR reaction.

Therefore, it is desirable to develop a reverse transcriptase
which acts at higher temperatures to overcome secondary structures in the template to avoid premature termination of the reaction and to assure the production of cDNA without deletions
which is active in the presence of magnesium ions in order to prepare cDNA from RNA templates with higher fidelity and
which has 3'-5'-exonuclease in order to remove misincorporated nucleotides before continuation of DNA synthesis and to produce products with low mutation frequency
which has a high specificity and produces exclusively or predominantly RT-PCR products derived from specific primer binding.

SUMMARY OF THE INVENTION

The present invention addresses these needs and provides a DNA polymerase mutant active at higher temperatures which has reverse transcriptase activity in the presence of magnesium ions and which has 3'-5' exonuclease activity and reduced or no 5'-3' exonuclease activity.

It is an object of this invention to provide a polymerase enzyme (EC 2.7.7.7.), characterized in that it has reverse transcriptase activity in the presence of magnesium ions as well as in the presence of manganese ions. In a further aspect the invention comprises a DNA polymerase having 3'-5'-exonuclease activity and reduced 5'-3' exonuclease activity. The enzyme according to the invention can be obtained from a polymerase obtainable from *Carboxydothermus hydrogenoformans* (Deutsche Sammlung von Mikroorganismen und Zellkulturen GmbH, Mascheroder Weg 1b, D-38124 Braunschweig, DSM No. 8979). In a further aspect the invention is directed to a DNA polymerase with reduced 5'-3' exonuclease activity having reverse transcriptase activity in the presence of magnesiums ions and in the substantial absence of manganese ions. In a further aspect the invention comprises a DNA polymerase having a molecular mass of about 64 to 71 kDa as determined by SDS PAGE analysis. The mutant polymerase enzyme with reduced 5'-3' exonuclease activity derived from a polymerase obtainable from *Carboxidothermus hydrogenoformans* is called hereinafter Δ Chy Polymerase.

In a further aspect the invention comprises a recombinant DNA sequence that encodes DNA polymerase activity of the Δ Chy Polymerase. In a related aspect, the DNA sequence is depicted as SEQ ID NO:10 (FIG. 1). In a second related aspect the invention comprises a recombinant DNA sequence that encodes essentially amino acid residues 1 to 607 (SEQ ID NO:11, FIG. 1). In a further aspect the invention comprises a recombinant DNA plasmid that comprises the DNA sequence of the invention inserted into plasmid vectors and which can be used to drive the expression of the Δ Chy DNA polymerase in a host cell transformed with the plasmid. In a further aspect the invention includes a recombinant strain comprising the vector pDS56 carrying the Δ Chy DNA polymerase gene and designated pΔ$_{2-225}$AR$_4$. The *E. coli* strain XL1 carrying the plasmid pΔ$_{2-225}$AR$_4$ was deposited on the Deutsche Sammlung von Mikroorganismen und Zeilkulturen GmbH, Mascherorder Weg 1b, D-38124 Braunschweig DSM No. 11854 (BMTU 7307) is designated *E. coli* GA1.

BRIEF DESCRIPTION OF THE DRAWINGS

FIG. 1 shows the nucleic acid and amino acid sequence of the "Klenow fragment" of Chy polymerase designated Δ Chy.

DETAILED DESCRIPTION OF THE INVENTION

In referring to a peptide chain as being comprised of a series of amino acids "substantially or effectively" in accordance with a list offering no alternatives within itself, we include within that reference any versions of the peptide chain bearing substitutions made to one or more amino acids in such a way that the overall structure and the overall function of the protein composed of that peptide chain is substantially the same as—or undetectably different to—that of the unsubstituted version. For example it is generally possible to exchange alanine and valine without greatly changing the properties of the protein, especially if the changed site or sites are at positions not critical to the morphology of the folded protein.

3'-5' exonuclease activity is commonly referred as "proofreading" or "editing" activity of DNA polymerases. It is located in the small domain of the large fragment of Type A polymerases. This activity removes mispaired nucleotides from the 3' end of the primer terminus of DNA in the absence of nucleoside triphosphates (Kornberg A. and Baker T. A. (1992) DNA Replication W. H. Freemann & Company, New York). This nuclease action is suppressed by deoxynucleoside triphosphates if they match to the template and can be incorporated into the polymer. The 3'-5' exonuclease activity of the claimed DNA polymerase can be measured as degradation or shortening of a 5'-digoxygenin-labeled oligonucleotide annealed to template DNA in the absence or presence of deoxyribonucleoside triphosphates or on DNA fragments in the absence or presence of deoxyribonucleoside triphosphates.

Figure 2:
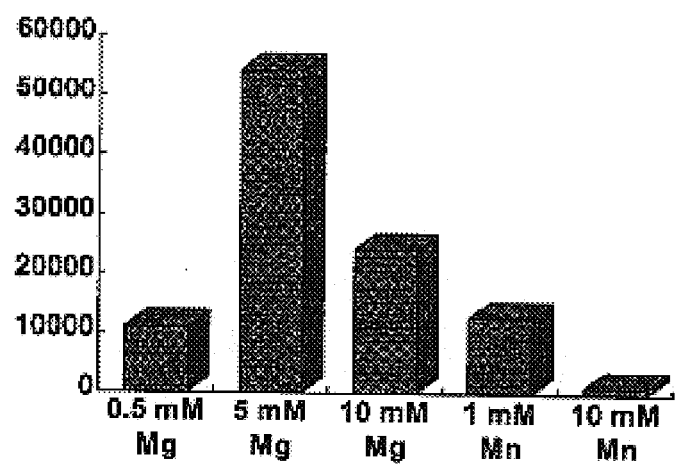
FIG. 2 shows the magnesium and manganese dependence of reverse transcriptase activity of Δ Chy.

*Carboxydothermus hydrogenoformans* DNA polymerase is the first DNA polymerase isolated from thermophilic eubacteria with a higher activity in the presence of magnesium ions than in the presence of manganese ions as shown in FIG. 2. The magnesium dependence of reverse transcriptase activity is advantageous since the DNA polymerase synthesize DNA with higher fidelity in the presence of magnesium than in the presence of manganese (Beckmann R.A. et al. (1985) *Biochemistry* 24, 5810–5817; Ricchetti M. and Buc H. (1993) *EMBO J.* 12, 387–396). Low fidelity DNA synthesis is likely to lead to mutated copies of the original template. In addition, $Mn^{2+}$ ions have been implicated in an increased rate of RNA degradation, particularly at higher temperatures and this can cause the synthesis of shortened products in the reverse transcription reaction.

The DNA sequence (SEQ ID NO:10) of Δ Chy polymerase and the derived amino acid sequence (SEQ ID NO:11) of the enzyme are shown in FIG. 1. The molecular weight deduced from the sequence is 70.3 kDa, in SDS polyacrylamide gel electrophoresis however Δ Chy polymerase has an electrophoretic mobility of approximately 65 kDa.

The Δ Chy DNA Polymerase has reduced 5'-3' exonuclease activity and has a temperature optimum at 72° C. and exhibits reverse transcriptase activity at temperatures between 50° C. and 75° C.

Figure 3:
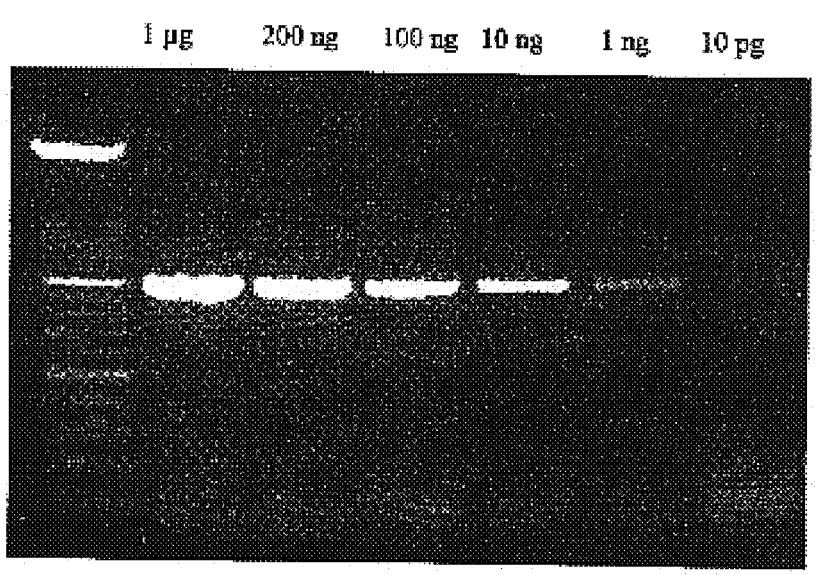
FIG. 3 shows the reverse transcription and amplification of a 997 bp fragment of the β-Actin gene from total mouse liver RNA using Δ Chy and the Expand HiFi-System and decreasing amounts of RNA.
Figure 4:
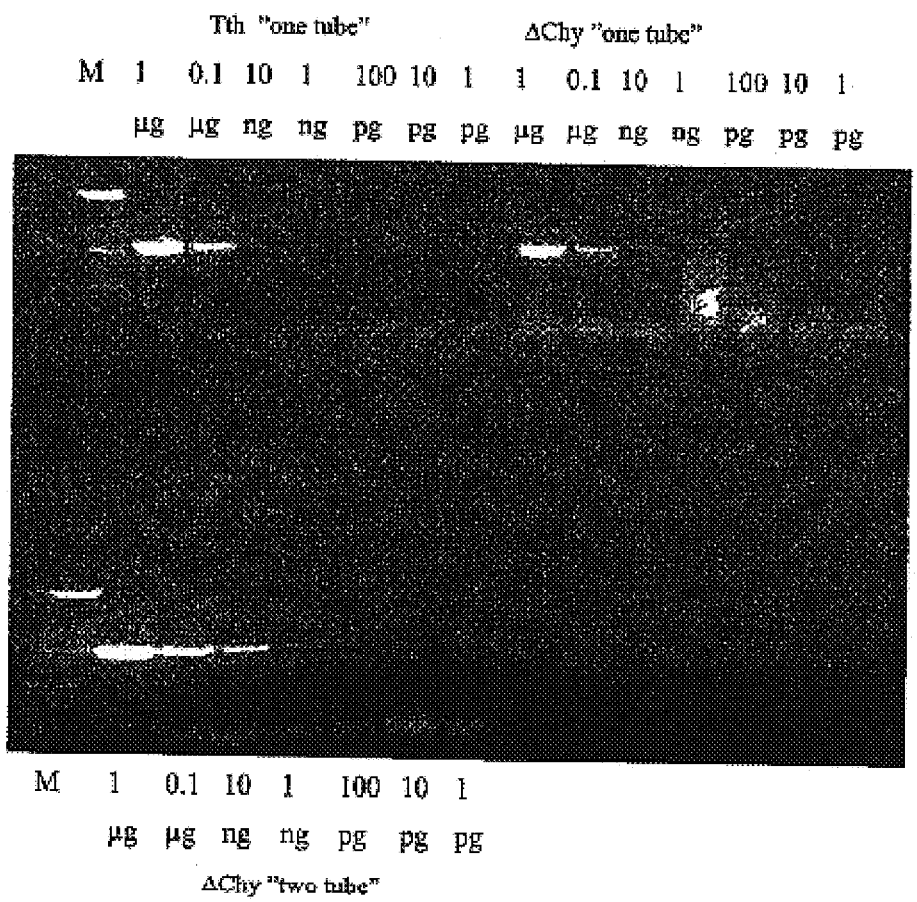
FIG. 4 shows the reverse transcription and amplification of a 997 bp fragment of β-actin from total mouse liver RNA in comparison to Tth polymerase. Reverse transcription was either coupled with amplification ("one tube") using the Expand HiFi-System from Boehringer Mannheim, or after reverse transcription the Expand HiFi-System from Boehringer Mannheim was added to the reaction mixture for the subsequent amplification reaction ("two tube").
Figure 5:
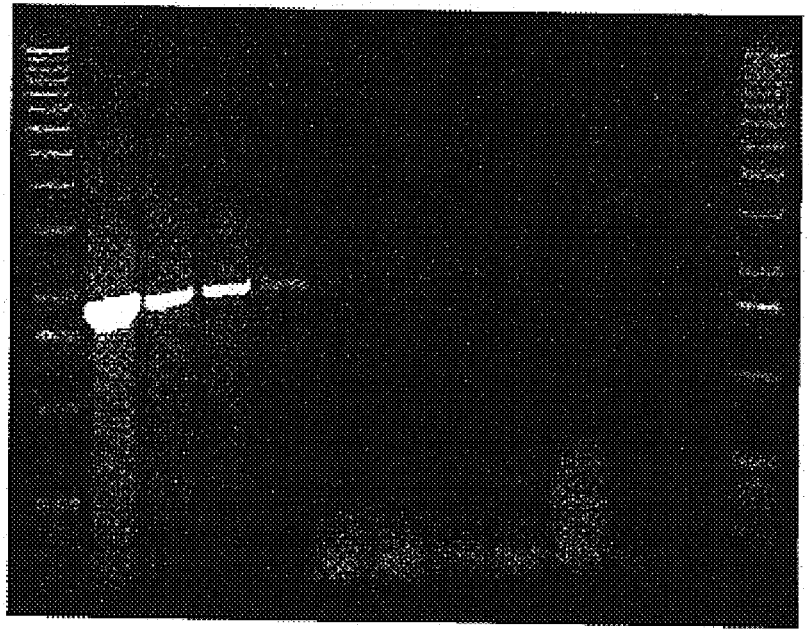
FIG. 5 shows the reverse transcription and amplification of a 1.83 kb fragment of Dystrophin from total human muscle RNA.

When using Δ Chy DNA Polymerase obtainable from *Carboxydothermus hydrogenoformans* having reduced 5'-3' exonuclease activity in RT-PCR as reverse transcriptase with subsequent PCR reaction using Taq-polymerase as PCR enzyme a remarkable high sensitivity is achieved (FIG. 3). The sensitivity of Δ Chy DNA Polymerase in RT-PCR is higher than the sensitivity of e.g. DNA polymerase from *Thermus thermophilus* (Tth polymerase) (Example 3, FIG. 4). Δ Chy DNA Polymerase also exhibits high sensitivity by amplifying a 1.83 kB fragment from total RNA from human muscle (FIG. 5). The error rate of Δ Chy DNA Polymerase is $1.58 \times 10^{-4}$ mutations per nucleotide per cycle and is therewith lower than the error rate of Tth Polymerase which is $2.37 \times 10^{-4}$ mutations per nucleotide per cycle. This results in higher fidelity of Δ Chy DNA polymerase in comparison to Tth Polymerase.

*Carboxydothermus hydrogenoformans* was isolated from a hot spring in Kamchatka by V. Svetlichny. A sample of *C. hydrogenoformans* was deposited on the Deutsche Sammlung von Mikroorganismen und Zellkulturen GmbH (DSM) under the terms of the Budapest Treaty and received Accession Number DSM 8979. The thermostable polymerase isolated from *Carboxydothermus hydrogenoformans* has a molecular weight of 100 to 105 KDa. The thermostable enzyme possesses 5'-3' polymerase activity, a 3'-5'-exonuclease activity and a reverse transcriptase-activity which is $Mg^{++}$-dependent. The thermostable enzyme may be native or recombinant and may be used for first- and second-strand cDNA synthesis, in cDNA cloning, DNA sequencing, DNA labeling and DNA amplification.

For recovering the native protein *C.hydrogenoformans* may be grown using any suitable technique, such as the technique described by Svetlichny et al. (1991) *System. Appl. Microbiol.* 14, 205–208. After cell growth one preferred method for isolation and purification of the enzyme is accomplished using the multi-step process as follows:

The cells are thawed, suspended in buffer A (40 mM Tris-HCl, pH 7.5, 0.1 mM EDTA, 7 mM 2-mercaptoethanol, 0.4 M NaCl, 10 mM Pefabloc) and lysed by twofold passage through a Gaulin homogenizer. The raw extract is cleared by centrifugation, the supernatant dialyzed against buffer B (40 mM Tris-HCl, pH 7.5, 0.1 mM EDTA, 7 mM 2-mercaptoethanol, 10% Glycerol) and brought onto a column filled with Heparin-Sepharose (Pharmacia). In each case the columns are equilibrated with the starting solvent and after the application of the sample washed with the threefold of its volume with this solvent. Elution of the first column is performed with a linear gradient of 0 to 0.5 M NaCl in Buffer B. The fractions showing polymerase activity are pooled and ammonium sulfate is added to a final concentration of 20%. This solution is applied to a hydrophobic column containing Butyl-TSK-Toyopearl (TosoHaas). The column is eluted with a falling gradient of 20 to 0% ammonium sulfate. The pool containing the activity is dialysed and again transferred to a column of DEAE-Sepharose (Pharmacia) and eluted with a linear gradient of 0–0.5 M NaCl in buffer B. The fourth column contains Tris-Acryl-Blue (Biosepra) and is eluted as in the preceding case. Finally the active fractions are dialyzed against buffer C (20 mM Tris-HCl, pH 7.5, 0.1 mM EDTA, 7.0 mM 2-mercaptoethanol, 100 mM NaCl, 50% Glycerol.

DNA polymerase activity was measured by incorporation of digoxigenin-labeled dUTP into the synthesized DNA and detection and quantification of the incorporated digoxigenin essentially according to the method described in Höltke, H.-J.; Sagner, G; Kessler, C. and Schmitz, G. (1992) *Biotechniques* 12, 104–113. The reaction is performed in a reaction volume of 50 µl containing 1 or 2 µl of diluted (0.05 U-0.01 U) DNA polymerase and 50 mM Tris-HCl, pH 8.5; 12.5 mM $(NH_4)_2SO_4$; 10 mM KCl; 5 mM $MgCl_2$; 10 mM 2-mercaptoethanol; 33 µM dNTPs; 200 µg/ml BSA; 12 µg of DNAse I-activated DNA from calf thymus and 0.036 µM digoxigenin-dUTP.

The samples are incubated for 30 min. at 72° C., the reaction is stopped by addition of 2 µl 0.5 M EDTA, and the tubes placed on ice. After addition of 8 µl 5 M NaCl and 150 µl of Ethanol (precooled to −20° C.) the DNA is precipitated by incubation for 15 min. on ice and pelleted by centrifugation for 10 min at 13000×rpm and 4° C. The pellet is washed with 100 µl of 70% Ethanol (precooled to −20° C.) and 0.2 M NaCl, centrifuged again and dried under vacuum.

The pellets are dissolved in 50 µl Tris-EDTA (10 mM/0.1 mM; pH 7.5). 5 µl of the sample are spotted into a well of a nylon membrane bottomed white microwave plate (Pall Filtrationstechnik GmbH, Dreieich, FRG, product no: SM045BWP). The DNA is fixed to the membrane by baking for 10 min. at 70° C. The DNA loaded wells are filled with 100 µl of 0.45 µm-filtrated 1% blocking solution (100 mM maleic acid, 150 mM NaCl, 1% (w/v) casein, pH 7.5). All following incubation steps are done at room temperature. After incubation for 2 min. the solution is sucked through the membrane with a suitable vacuum manifold at −0.4 bar. After repeating the washing step, the wells are filled with 100 µl of a 1:10,000-dilution of Anti-digoxigenin-AP, Fab fragments (Boehringer Mannheim, FRG, no: 1093274) diluted in the above blocking solution. After incubation for 2 min. and sucking this step is repeated once. The wells are washed twice under vacuum with 200 µl each time washing-buffer 1 (100 mM maleic-acid, 150 mM NaCl, 0.3%(v/v) Tween™ 20, pH 7.5). After washing another two times under vacuum with 200 µl each time washing-buffer 2 (10 mM Tris-HCl, 100 mM NaCl, 50 mM $MgCl_2$, pH 9.5) the wells are incubated for 5 min. with 50 µl of CSPD™ (Boehringer Mannheim, no: 1655884), diluted 1:100 in washing-buffer 2, which serves as a chemiluminescent substrate for the alkaline phosphatase. The solution is sucked through the membrane and after 10 min. incubation the RLU/s (Relative Light Unit per second) are detected in a Luminometer e.g. MicroLumat LB 96 P (EG&G Berthold, Wilbad, FRG).

With a serial dilution of Taq DNA polymerase a reference curve is prepared from which the linear range serves as a standard for the activity determination of the DNA polymerase to be analyzed.

The production of a recombinant form of *Carboxydothermus hydrogenoformans* DNA polymerase generally includes the following steps: chromosomal DNA from *Carboxydothermus hydrogenoformans* is isolated by treating the cells with detergent e.g. SDS and a proteinase e.g. Proteinase K. The solution is extracted with phenol and chloroform and the DNA purified by precipitation with ethanol. The DNA is dissolved in Tris/EDTA buffer and the gene encoding the DNA polymerase is specifically amplified by the PCR technique using two mixed oligonucleotides (primer 1 and 2). These oligonucleotides, described by SEQ ID NO:1 and SEQ ID NO:2 were designed on the basis of conserved regions of family A DNA polymerases as published by Braithwaite D.K. and Ito J. (1993) *Nucl. Acids Res.* 21, 787–802. The specifically amplified fragment is ligated into a vector, preferably the pCR™II vector (Invitrogen) and the sequence is determined by cycle-sequencing. Complete isolation of the coding region and the flanking sequences of the DNA polymerase gene can be performed by restriction fragmentation of the *Carboxydothermus hydrogenoformans* DNA with another restriction enzyme as in the first round of screening and by inverse PCR (Innis et al., (1990) PCR Protocols; Academic Press, Inc., 219–227). This can be accomplished with synthesized oligonucleotide primers binding at the outer DNA sequences of the gene part but in opposite orientation. These oligonucleotides described by SEQ ID NO:3 and 4, were designed on the basis of the sequences which were determined by sequencing of the first PCR product described above. As template DNA from *Carboxydothermus hydrogenoformans* is used which is cleaved by restriction digestion and circularized by contacting with T4 DNA ligase. To isolate the coding region of the entire polymerase gene, another PCR is performed using primers as shown in SEQ ID NO:5 and 6. The complete DNA polymerase gene is amplified directly from genomic DNA with primers suitable for introducing ends compatible with the linearized expression vector.

```
SEQ ID NO:1:
Primer 1: 5'-CCN AAY YTN CAR AAY ATH-3'

SEQ ID NO:2:
Primer 2: 5'-YTC RTC RTG NAC YTG-3'

SEQ ID NO:3:
Primer 3: 5'-GGG CGA AGA CGC TAT ATT CCT GAG C-3'

SEQ ID NO:4:
Primer 4: 5'-GAA GCC TTA ATT CAA TCT GGG AAT AAT C-3'

SEQ ID NO:5:
Primer 5: 5'-CGA ATT CAA TCC ATG GGA AAA GTA GTC CTG GTG GAT-3'

SEQ ID NO:6:
Primer 6: 5'-CGA ATT CAA GGA TCC TTA CTT CGC TTC ATA CCA GTT-3'
```

The Determination of reverse transcriptase activity is performed essentially as described for determination of DNA polymerase activity except that the reaction mixture consists of the following components: 1 µg of polyA-$(dT)_{15}$, 33 µM of dTTP, 0.36 µM of digoxigenin-dUTP, 200 mg/ml BSA, 10 mM Tris-HCl, pH 8.5, 20 mM KCl, 5 mM $MgCl_2$, 10 mM DTE and various amounts of DNA polymerase. The incubation temperature used is 50° C.

Isolation of recombinant DNA polymerase from *Carboxydothermus hydrogenoformans* may be performed with the same protocol or with other commonly used procedures.

The gene is operably linked to appropriate control sequences for expression in either prokaryotic or eucaryotic host/vector systems. The vector preferably encodes all functions required for transformation and maintenance in a suitable host, and may encode selectable markers and/or control sequences for polymerase expression. Active recombinant thermostable polymerase can be produced by transformed host cultures either continuously or after induction of expression. Active thermostable polymerase can be recovered either from host cells or from the culture media if the protein is secreted through the cell membrane.

The use of a plasmid as an appropriate vector has shown to be advantageous, particularly pDS56 (Stüber, D., Matile, H. and Garotta, G. (1990) Immunological Methods, Letkovcs, I. and Pernis, B., eds). The plasmid carrying the Carboxydothermus hydrogenoformans DNA polymerase gene is then designated pAR4.

According to the present invention the use of the E. coli strain BL21 (DE3) pUBS520 (Brinkmann et al., (1989) Gene 85, 109–114) has shown to be advantageous. The E.coli strain BL 21 (DEB) pUBS 520 transformed with the plasmid pAR4 is then designated AR96 (DSM No 11179).

The mutant ΔChy was obtained by deletion of an N-terminal fragment of the recombinant wild type Carboxydothermus hydrogenoformans DNA polymerase using inverse PCR (Innis et al., (1990) PCR Protocols; Academic Press, Inc., p 219–227). The reverse primer used is complementary to the cloning site of the expression vector pDS56 (Stüber, D., Matile, H. and Garotta, G. (1990) Immunological Methods, Letkovcs, I. and Pernis, B., eds.) at the Nco I restriction site (bases 120–151) and has the sequence:
SEQ ID NO:7:
Primer 7: 5'-CGG TAA ACC CAT GGT TAA TTT CTC CTC TTT AAT GAA TTC-3'.

This primer contains additional 7 bases at the 5' end to ensure a better binding of the Nco I restriction enzyme in the subsequent restriction enzyme cleavage. The second (forward) primer was complementary to bases 676–702 of the wild type gene and has the sequence:
SEQ ID NO:8:
Primer 8: 5'-CGG GAA TCC ATG GAA AAG CTT GCC GAA CAC GAA AAT TTA-3'

Figure 7:
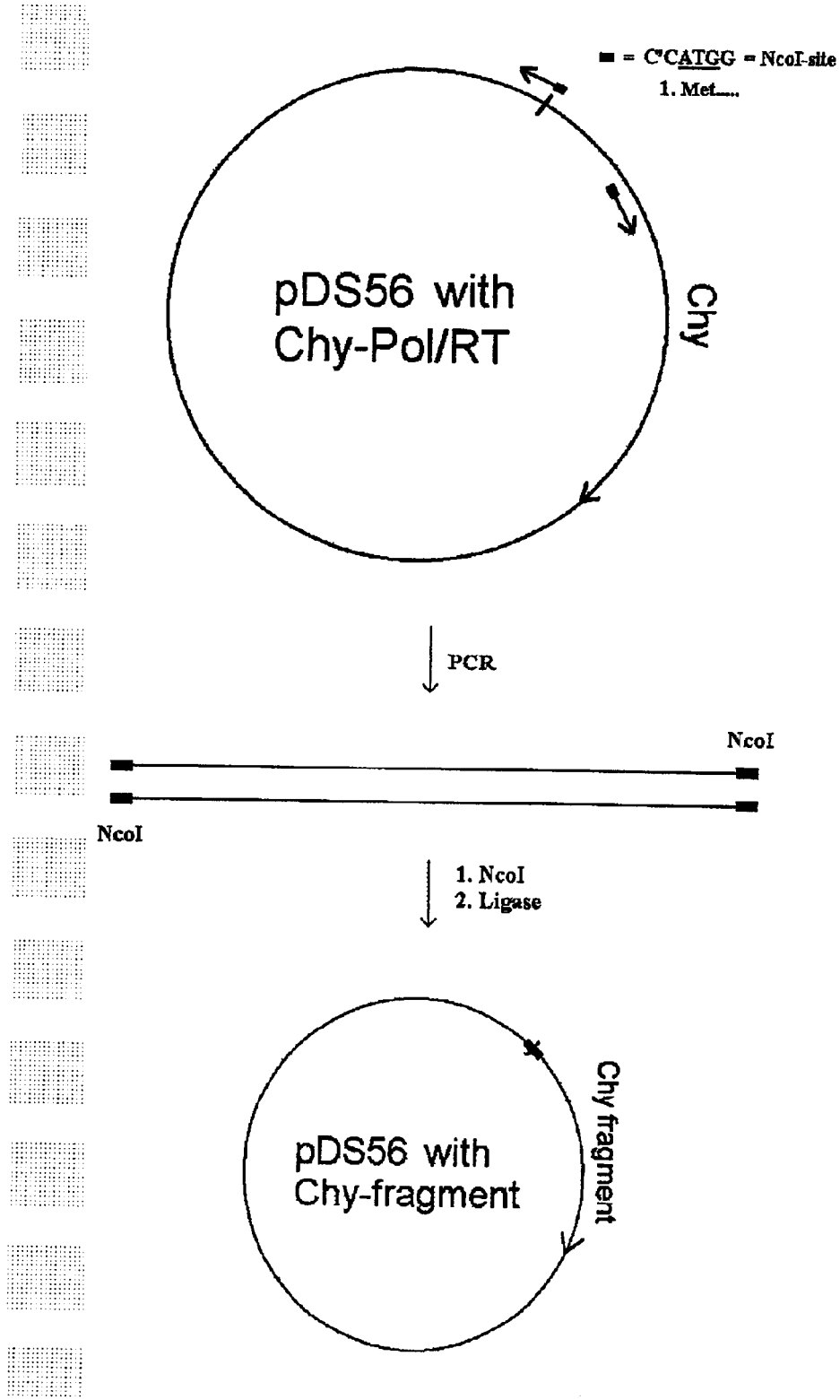
FIG. 7 shows schematically the construction of the clone encoding Δ Chy from the clone encoding the wild type gene.

The forward primer also contained an additional Nco I restriction site and additional 7 bases at the 5' end. Plasmid pDS56 DNA containing the poymerase-gene of Carboxydothermus hydrogenoformans at the Nco I/BamHI restriction sites was used as template for PCR. The PCR reaction was performed on the circular plasmid DNA pAR4. The fragment encoding the mutated Carboxydothermus hydrogenoformans DNA polymerase (Δ Chy) and the vector DNA were amplified as linear DNA by PCR using the Expand High Fidelity PCR System (Boebringer Mannheim) according to the supplier's specifications (FIG. 7). The length of the gene encoding Δ Chy is 1821 bp.

Amplification (Perkin Elmer GeneAmp 9600 thermocycler) was carried out with the following conditions: 2 min 94° C., (10 sec 94° C.; 30 sec 65° C.; 4 min 68° C.)×10; (10 sec 94° C.; 30 sec 65° C.; 4 min 68° C.)+ cycle elongation of 20 sec for each cycle)×20; 7 min 72° C.; After PCR the amplified DNA was purified using the High Pure PCR Product Purification Kit (Boehringer Mannheim) and digested with NcoI (3U/μg DNA) for 16 h (Boehringer Mannheim) according to the supplier's specifications.

For extraction with Phenol/Chloroform/Isoamylalcohol (24:24:1) the volume of the sample was raised to 100 μl with TE. After extraction the DNA was precipitated by adding ⅒ volumes of 3M Sodium Acetate, pH 5.2 and 2 volumes of EtOH. The DNA was circularized using the Rapid DNA Ligation Kit (Boehringer Mannheim) according to the supplier's specification. The ligated products were introduced into E. coli XL1-Blue by transformation according to the procedure of Chung, C. T. et al. (1989) Proc. Natl. Acad. Sci. USA 86, 2172–2175. Transformants were plated on L-agar containing 100 μg/ml ampicillin to allow selection of recombinants. Colonies were picked and grown in L-broth containing 100 μg/ml ampicillin. Plasmid DNA was prepared with the High Pure Plasmid Isolation Kit (Boehringer Mannheim) according to the supplier's specification. The plasmids were screened for insertions by digestion with NcoI/BamHI. Strains containing the genes of interest were grown in L-broth supplemented with 100 μg/ml ampicillin and tested for the expression of DNA polymerase/reverse transcriptase activity by induction of exponentially growing culture with 1 mM IPTG and assaying the heat-treated extracts (72° C.) for DNA polymerase/reverse transcriptase activity as described above (determination of DNA polymerase activity and determination of reverse transcriptase activity).

The present invention provides improved methods for efficiently transcribing RNA and amplifying RNA or DNA. These improvements are achieved by the discovery and application of previously unknown properties of thermoactive DNA polymerases with reverse transcriptase activity.

The enzyme of this invention may be used for any purpose in which such enzyme activity is necessary or desired. In a particularly preferred embodiment, the enzyme catalyzes reverse transcription of RNA which is amplified as DNA by a second DNA polymerase present in the amplification reaction known as RT-PCR (Powell et al. (1987) Cell 50, 831–840). Any ribonucleic acid sequence, in purified or nonpurified form, can be utilized as the starting nucleic acid(s), provided it contains or is suspected to contain the specific nucleic acid sequence desired. The nucleic acid to be amplified can be obtained from any source, for example, from plasmids such as pBR322, from cloned RNA, from natural RNA from any source, including bacteria, yeast, viruses, organelles, and higher organisms such as plants and animals, or from preparations of nucleic acids made in vitro.

RNA may be extracted from blood, tissue material such as chorionic villi, or amniotic cells by a variety of techniques. See, e.g., Maniatis et al., (1982) Molecular Cloning: A Laboratory Manual (Cold Spring Harbor Laboratory, Cold Spring Harbor, N.Y.) pp. 280–281. Thus the process may employ, for example, RNA, including messenger RNA, which RNA may be single-stranded or double-stranded. In addition, a DNA-RNA hybrid which contains one strand of each may be utilized.

The amplification of target sequences from RNA may be performed to prove the presence of a particular sequence in the sample of nucleic acid to be analyzed or to clone a specific gene. Δ Chy DNA polymerase is very useful for these processes. Due to its 3'-5' exonuclease activity it is able to synthesize products with higher accuracy than the reverse transcriptase of the state of the art.

Δ Chy DNA polymerase may also be used to simplify and improve methods for detection of RNA target molecules in a sample. In these methods Δ Chy DNA polymerase from Carboxydothermus hydrogenoformans may catalyze: (a) reverse transcription and (b) second strand cDNA synthesis. The use of DNA polymerase from Carboxydothermus hydrogenoformans may be used to perform RNA reverse transcription and amplification of the resulting complementary DNA with enhanced specificity and with fewer steps than previous RNA cloning and diagnostic methods.

Another aspect of the invention comprises a kit for performing RT-PCR comprising Δ Chy polymerase, reaction buffers, nucleotide mixtures, and optionally a thermostable DNA polymerase for detection and amplification of RNA either in a one step reaction or for reverse transcription of the template RNA and subsequent amplification of the cDNA product.

The following examples describe the invention in greater detail:

EXAMPLE 1

Figure 6:
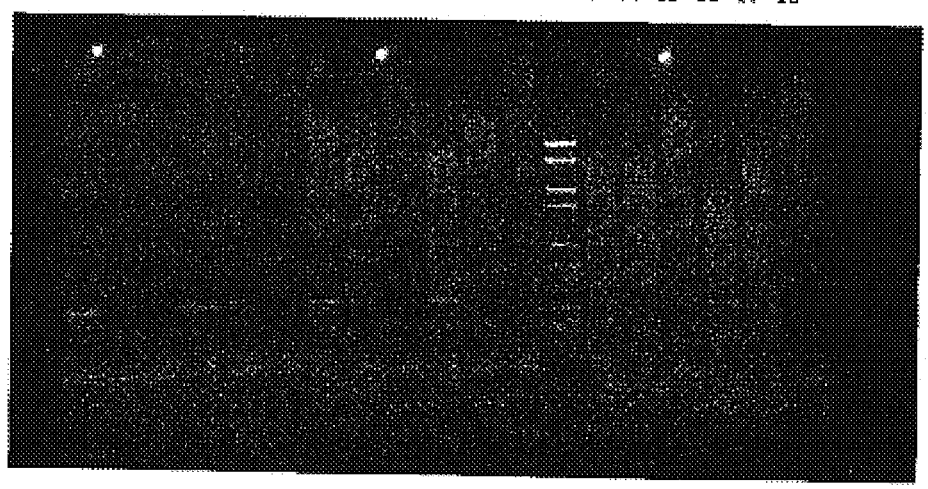
FIG. 6 shows the reverse transcription and amplification of a 324 bp fragment of β-actin from total mouse liver RNA with various amounts of Chy polymerase and various incubation times.

Reverse Transcription of a 324 bp β-Actin Fragment with Chy Wild Type DNA Polymerase Used as Reverse Transcriptase Followed by PCR with Taq-Polymerase (FIG. 6).

The reaction mixture (20 μl) contained 200 ng total mouse liver RNA, 200 μM dNTP, 10 mM Tris-HCl, pH 8.8, 5 mM DTT, 10 mM 2-mercaptoethanol, 15 mM KCl, 4.5 mM MgCl$_2$, 0.02 mg/ml BSA, 20 pmol of reverse primer (β-actin reverse: 5'-AAT TCG GAT GGC TAC GTA CAT GGC TG-3' [SEQ ID NO: 9]) and Chy-polymerase 33 units (lanes 1, 4, 7, 10, 13, 16), 13.2 units (lanes 2, 5, 8, 11, 14, 17) and 6.6 units (lanes 3, 6, 9, 12, 15, 18). Reactions were incubated for 5 min (lanes 1 to 6), 10 min (lanes 7 to 12) and 15 min (lanes 13 to 18) at 70° C. 20 μl of the reverse transcription reaction was used as template for PCR (100 μl reaction volume) with Taq-polymerase (Boehringer Mannheim) according to the supplier's specification using 20 pmol of forward and reverse primer (Primer sequence "β-actin forward": 5'AGC TTG CTG TAT TCC CCT CCA TCG TG-3' [SEQ ID NO: 12], primer sequence "β-actin reverse": 5'-AAT TCG GAT GGC TAC GTA CAT GGC TG-3' [SEQ ID NO: 9]) and 200 μM dNTP's. Amplification was carried out using the following temperature profile: 2 min 94° C.; (10 sec 94° C.; 30 sec 60° C.; 30 sec 72° C.)×30; 7 min 72° C.

EXAMPLE 2
Construction of the Vector Expressing Δ Chy.

The mutant was obtained by deletion of an N-terminal fragment of recombinant wild type *Carboxydothermus hydrogenoformans* DNA polymerase using inverse PCR (Innis et al., (1990) PCR Protocols; Academic Press, Inc., p 219–227). The reverse primer used is complementary to the cloning site of the expression vector pDS56 (Stüber, D., Matile, H. and Garotta, G. (1990) Immunological Methods, Letkovcs, I. and Pernis, B., eds.) at the Nco I restriction site (bases 120–151) and has the sequence: 5'-CGG TAA ACC CAT GGT TAA TTT CTC CTC TTT AAT GAA TTC-3' (SEQ ID NO: 7). This primer contains additional 7 bases at the 5' end to ensure a better binding of the Nco I restriction enzyme in the subsequent restriction enzyme cleavage. The second (forward) primer, was complementary to bases 676–702 of the wild type gene (sequence: 5'-CGG GAA TCC ATG GAA AAG CTT GCC GAA CAC GAA AAT TTA-3' [SEQ ID NO: 8]). The forward primer also contained an additional Nco I restriction site and additional 7 bases at the 5'-end. Plasmid pDS56 DNA containing the polymerase-gene of *Carboxydothermus hydrogenoformans* at the Nco I/BamHI restriction sites was used as template for PCR. The PCR reaction was performed on circular plasmid DNA pAR4. The fragment of *Carboxydothermus hydrogenoformans* DNA polymerase (ΔChy) and the vector DNA were amplified as linear DNA by PCR using the Expand High Fidelity PCR System (Boehringer Mannheim) according to the supplier's specifications. The length of the gene encoding Δ Chy is 1821 bp. Amplification (Perkin Elmer Gene-Amp 9600 thermocycler) was carried out with the following conditions: 2 min 94° C., (10 sec 94° C.; 30 sec 65° C.; 4 min 68° C.)×10; (10 sec 94° C.; 30 sec 65° C.; 4 min 68° C.)+cycle elongation of 20 sec for each cycle)×20; 7 min 72° C.

After PCR the amplified DNA was purified using the High Pure PCR Product Purification Kit (Boehringer Mannheim) and digested with NcoI (3U/μg DNA) for 16 h (Boehringer Mannheim) according to the supplier's specifications. For extraction with Phenol/Chloroform/Isoamylalcohol (24:24:1) the volume of the sample was raised to 100 μl with TE. After extraction the DNA was precipitated by adding ¹⁄₁₀ volumes of 3M Sodium Acetate, pH 5.2 and 2 volumes of EtOH. The DNA was circularized using the Rapid DNA Ligation Kit (Boehringer Mannheim) according to the supplier's specification. The ligated products were introduced into *E. coli* XL1-Blue by transformation according to the procedure of Chung, C. T. et al. (1989) *Proc. Natl. Acad. Sci. USA* 86, 2172–2175. Transformants were plated on L-agar containing 100 μg/ml ampicillin to allow selection of recombinants. Colonies were picked and grown in L-broth containing 100 μg/ml ampicillin. Plasmid DNA was prepared with the High Pure Plasmid Isolation Kit (Boehringer Mannheim) according to the supplier's specification. The plasmids were screened for insertions by digestion with NcoI/BamHI. Strains containing the genes of interest were grown in L-broth supplemented with 100 μg/ml ampicillin and tested for the expression of DNA polymerase/reverse transcriptase activity by induction of exponentially growing culture with 1 mM IPTG and assaying the heat-treated extracts (72° C.) for DNA polymerase/reverse transcriptase activity as described above (determination of DNA polymerase activity and determination of Reverse Transcriptase activity). (FIG. 7)

EXAMPLE 3
Reverse Transcription and Amplification of a 997 bp Fragment of β-actin from Total Mouse Liver RNA. Comparison of Δ Chy with Tth Polymerase in the Reverse Transcription Reaction (FIG. 4) Either in a Coupled RT-PCR Reaction ("one tube") or in Consecutive Steps, Reverse Transcription, Addition of Polymerase and Amplification of the cDNA Product of the First Step.
"One Tube" System:

The reactions (50 μl) contained 10 mM Tris-HCl, pH 8.8 at 25° C., 15 mM KCl, 2.5 mM MgCl$_2$, 400 μM of each dNTP, decreasing amounts of mouse total RNA (Clonetech) as indicated in the figure, 300 nM of each primer, 60 units of Δ Chy and 3.5 units of the Expand HiFi enzyme mix (Boehringer Mannheim GmbH). All reactions were incubated at 60° C. for 30 min (RT step). Amplification followed immediately with following cycle profile (Perkin Elmer GeneAmp 9600 thermocycler): 30 sec. at 94° C.; (30 sec at 94° C., 30 sec at 60° C., 1 min. at 68° C.)×10; (30 sec. at 94° C., 30 sec. at 60° C., 1 min. at 68° C.+cyle elongation of 5 sec. for each cycle)×20; 7 min at 68° C.;
"Two Tube" System:

Reverse transcription is performed in 10 mM Tris-HCl, pH 8.8, 15 mM (NH$_4$)$_2$SO$_4$, 0.1% Tween, 4.5 mM MgCl$_2$, 2% DMSO, 800 μM dNTPs, 300 nmoles of each primer, 60 units of Δ Chy, various amounts of total mouse muscle RNA as indicated in the figure. The reaction was performed in a volume of 25 μl for 30 min at 60° C. 5 μl of this reaction are used for the amplification with the Expand HiFi-system from Boehringer Mannheim. Amplification was performed with 2.6 units of polymerase mixture in a reaction volume of 25 μl. The following temperature cycling conditions were used: 30 sec. at 94° C., (30 sec. at 94° C., 30 sec at 60° C., 1 min at 68° C.)×10, (30 sec. at 94° C., 30 sec. at 60° C., 1 min at 68° C.+cycle elongation for 5 sec for each cycle)×20.

As a control reaction the same template-primer system was used for RT-PCR with Tth polymerase (Boehringer Mannheim). The reaction was set up according to the supplier's specifications for the "one step" variant.

LITERATURE CITED

Beckmann R. A. et al. (1985) *Biochemistry* 24, 5810–5817
Berger et al., (1983) *Biochemistry* 22, 2365–2372
Bessmann et al. (1957) *J. Biol. Chem.* 233, 171–177
Braithwaite D. K. and Ito J. (1993) *Nucl. Acids Res.* 21, 787–802
Brinkmann U. et al. (1989) *Gene* 85, 109–114.
Brock et al. (1969) *J. Bacteriol.* 98, 289–297

Buttin and Kornberg (1966) *J. Biol. Chem.* 241, 5419–5427
Chung, C. T. et al. (1989) *Proc. Natl. Acad. Sci. USA* 86, 2172–2175
Engelke et al. (1990) *Anal. Biochem.* 191, 396–400.
Gulati et al. (1974) *Proc. Nat. Acad. Sci. USA* 71, 1035–1039
Höltke, H.-J.; Sagner, G; Kessler, C. and Schmitz, G. (1992) *Biotechniques* 12, 104–113.
Innis et al., (1990) PCR Protocols; Academic Press, Inc., 219–227
Kaledin et al. (1980), *Biokhimiya* 45, 644–651.
Kaledin et al. (1981) *Biokhimiya* 46, 1576–1584.
Kaledin et al. (1982) *Biohkimiya* 47, 1785–1791.
Karkas (1973) *Proc. Nat. Acad. Sci.* USA 70, 3834–3838
Kornberg A. and Baker T. A. (1992) *DNA Replication* W. H. Freemann & Company, New York.
Lawyer et al. (1989) *J. Biol. Chem.* 264, 6427–6437.
Lundberg et al. (1991) *Gene* 108, 1–6.
Maniatis et al. (1982) *Molecular Cloning: A Laboratory Manual*, Cold Spring Harbor, N.Y.
Neuner et al. (1990) *Arch. Microbiol.* 153, 205–207.
Powell et al. (1987) *Cell* 50, 831–840
Perbal (1984), A Practical Guide to Molecular Cloning, Wiley & Sons New York
Perler et al. (1992) *Proc. Natl. Acad. Sci USA* 89, 5577–5581.
Powell et al. (1987) *Cell* 50, 831–840
Ricchetti M. and Buc H. (1993) *EMBO J.* 12, 387–396.
Ruttimann et al. (1985) *Eur. J. Biochem.* 149, 41–46.
Saunders and Saunders (1987) Microbial Genetics Applied to Biotechnology, Croom Helm, London
Spanos A. and Hübscher U. (1983) *Methods in Enzymology* 91, 263–277.
Stüber D., Matile H. and Garotta G. (1990) *Immunological Methods*, Letkovcs, I and Pernis, B., eds.
Svetlichny et al. (1991) *System. Appl. Microbiol.,* 14, 205–208.
Triglia T. et al. (1988) *Nucleic Acids Res.* 16, 8186.
Verma (1977) *Biochem. Biophys. Acta* 473, 1
Wittig and Wittig, (1978) *Nuc. Acids Res.* 5, 1165–1178

We claim:

1. An isolated DNA sequence encoding SEQ ID NO:11.
2. The DNA sequence of claim 1 that comprises SEQ ID NO:10.
3. A vector comprising the DNA sequence of claim 1.
4. A vector comprising the DNA sequence of claim 2.
5. The vector of claim 4 that is $p\Delta_{2-225}AR_4$.
6. A host cell transformed with the vector of claim 3.
7. A host cell transformed with the vector of claim 4.
8. A host cell transformed with the vector of claim 5.
9. The host cell of claim 8 that is *E. coli* GA1.

* * * * *

SEQUENCE LISTING

<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: Description of artificial sequence:
      amplification primer
<221> NAME/KEY: misc_feature
<222> LOCATION: (3)..(3)
<223> OTHER INFORMATION: any nucleotide
<221> NAME/KEY: misc_feature
<222> LOCATION: (9)..(9)
<223> OTHER INFORMATION: any nucleotide

<400> SEQUENCE: 1
ccnaayytnc araayath                                                 18

<210> SEQ ID NO 2
<211> LENGTH: 15
<212> TYPE: DNA
<213> ORGANISM: Artificial Sequence
<220> FEATURE:
<223> OTHER INFORMATION: Description of artificial sequence:
      amplification primer
<221> NAME/KEY: misc_feature
<222> LOCATION: (10)..(10)
<223> OTHER INFORMATION: any nucleotide

<400> SEQUENCE: 2
ytcrtcrtgn acytg                                                    15

<210> SEQ ID NO 3
<211> LENGTH: 25
<212> TYPE: DNA
<213> ORGANISM: Artificial Sequence
<220> FEATURE:
<223> OTHER INFORMATION: Description of artificial sequence:
      amplification primer

<400> SEQUENCE: 3
gggcgaagac gctatattcc tgagc                                         25

```
<210> SEQ ID NO 4
<211> LENGTH: 28
<212> TYPE: DNA
<213> ORGANISM: Artificial Sequence
<220> FEATURE:
<223> OTHER INFORMATION: Description of artificial sequence:
      amplification primer

<400> SEQUENCE: 4
gaagccttaa ttcaatctgg gaataatc                                      28

<210> SEQ ID NO 5
<211> LENGTH: 36
<212> TYPE: DNA
<213> ORGANISM: Artificial Sequence
<220> FEATURE:
<223> OTHER INFORMATION: Description of artificial sequence:
      amplification primer

<400> SEQUENCE: 5
cgaattcaat ccatgggaaa agtagtcctg gtggat                             36

<210> SEQ ID NO 6
<211> LENGTH: 36
<212> TYPE: DNA
<213> ORGANISM: Artificial Sequence
<220> FEATURE:
<223> OTHER INFORMATION: Description of artificial sequence:
      amplification primer

<400> SEQUENCE: 6
cgaattcaag gatccttact tcgcttcata ccagtt                             36

<210> SEQ ID NO 7
<211> LENGTH: 39
<212> TYPE: DNA
<213> ORGANISM: Artificial Sequence
<220> FEATURE:
<223> OTHER INFORMATION: Description of artificial sequence:
      amplification primer

<400> SEQUENCE: 7
cggtaaaccc atggttaatt tctcctcttt aatgaattc                          39

<210> SEQ ID NO 8
<211> LENGTH: 39
<212> TYPE: DNA
<213> ORGANISM: Artificial Sequence
<220> FEATURE:
<223> OTHER INFORMATION: Description of artificial sequence:
      amplification primer

<400> SEQUENCE: 8
cgggaatcca tggaaaagct tgccgaacac gaaaattta                          39

<210> SEQ ID NO 9
<211> LENGTH: 26
<212> TYPE: DNA
<213> ORGANISM: Artificial Sequence
<220> FEATURE:
<223> OTHER INFORMATION: Description of artificial sequence:
      amplification primer

<400> SEQUENCE: 9
aattcggatg gctacgtaca tggctg                                        26

<210> SEQ ID NO 10
```

-continued

```
<211> LENGTH: 1824
<212> TYPE: DNA
<213> ORGANISM: Carboxydothermus hydrogenoformans
<220> FEATURE:
<221> NAME/KEY: CDS
<222> LOCATION: (1)..(1824)

<400> SEQUENCE: 10
```

| | | | | | | | | | | | | | | | | |
|---|---|---|---|---|---|---|---|---|---|---|---|---|---|---|---|---|
| atg | aaa | aag | ctt | gcc | gaa | cac | gaa | aat | tta | gca | aaa | ata | tcg | aaa | caa | 48 |
| Met | Glu | Lys | Leu | Ala | Glu | His | Glu | Asn | Leu | Ala | Lys | Ile | Ser | Lys | Gln | |
| 1 | | | | 5 | | | | | 10 | | | | | 15 | | |
| tta | gct | aca | atc | ctg | cgg | gaa | ata | ccg | tta | gaa | atc | tcc | ctg | gaa | gat | 96 |
| Leu | Ala | Thr | Ile | Leu | Arg | Glu | Ile | Pro | Leu | Glu | Ile | Ser | Leu | Glu | Asp | |
| | | | 20 | | | | | 25 | | | | | 30 | | | |
| tta | aaa | gtt | aaa | gaa | cct | aat | tat | gaa | gaa | gtt | gct | aaa | tta | ttt | ctt | 144 |
| Leu | Lys | Val | Lys | Glu | Pro | Asn | Tyr | Glu | Glu | Val | Ala | Lys | Leu | Phe | Leu | |
| | | | 35 | | | | | 40 | | | | | 45 | | | |
| cac | ctt | gag | ttt | aaa | agc | ttt | tta | aaa | gaa | ata | gaa | cca | aaa | ata | aag | 192 |
| His | Leu | Glu | Phe | Lys | Ser | Phe | Leu | Lys | Glu | Ile | Glu | Pro | Lys | Ile | Lys | |
| | 50 | | | | | 55 | | | | | 60 | | | | | |
| aaa | gaa | tac | cag | gaa | ggt | aaa | gat | ttg | gtg | caa | gtt | gaa | act | gta | gaa | 240 |
| Lys | Glu | Tyr | Gln | Glu | Gly | Lys | Asp | Leu | Val | Gln | Val | Glu | Thr | Val | Glu | |
| 65 | | | | | 70 | | | | | 75 | | | | | 80 | |
| acg | gaa | gga | cag | att | gca | gta | gtt | ttt | agt | gat | gga | ttt | tat | gtt | gat | 288 |
| Thr | Glu | Gly | Gln | Ile | Ala | Val | Val | Phe | Ser | Asp | Gly | Phe | Tyr | Val | Asp | |
| | | | | 85 | | | | | 90 | | | | | 95 | | |
| gac | ggg | gaa | aaa | aca | aag | ttt | tac | tct | tta | gac | cgg | ctg | aat | gaa | ata | 336 |
| Asp | Gly | Glu | Lys | Thr | Lys | Phe | Tyr | Ser | Leu | Asp | Arg | Leu | Asn | Glu | Ile | |
| | | | 100 | | | | | 105 | | | | | 110 | | | |
| gag | gaa | ata | ttt | agg | aat | aaa | aaa | att | att | acc | gac | gat | gcc | aaa | gga | 384 |
| Glu | Glu | Ile | Phe | Arg | Asn | Lys | Lys | Ile | Ile | Thr | Asp | Asp | Ala | Lys | Gly | |
| | | | 115 | | | | | 120 | | | | | 125 | | | |
| att | tat | cat | gtc | tgt | tta | gaa | aaa | ggt | ctg | act | ttt | ccc | gaa | gtt | tgt | 432 |
| Ile | Tyr | His | Val | Cys | Leu | Glu | Lys | Gly | Leu | Thr | Phe | Pro | Glu | Val | Cys | |
| | 130 | | | | | 135 | | | | | 140 | | | | | |
| ttt | gat | gcg | cgg | att | gca | gct | tat | gtt | tta | aac | ccg | gcc | gac | caa | aat | 480 |
| Phe | Asp | Ala | Arg | Ile | Ala | Ala | Tyr | Val | Leu | Asn | Pro | Ala | Asp | Gln | Asn | |
| 145 | | | | | 150 | | | | | 155 | | | | | 160 | |
| ccc | ggc | ctc | aag | ggg | ctt | tat | cta | aag | tat | gac | tta | ccg | gtg | tat | gaa | 528 |
| Pro | Gly | Leu | Lys | Gly | Leu | Tyr | Leu | Lys | Tyr | Asp | Leu | Pro | Val | Tyr | Glu | |
| | | | | 165 | | | | | 170 | | | | | 175 | | |
| gat | gta | tct | tta | aac | att | aga | ggg | ttg | ttt | tat | tta | aaa | aaa | gaa | atg | 576 |
| Asp | Val | Ser | Leu | Asn | Ile | Arg | Gly | Leu | Phe | Tyr | Leu | Lys | Lys | Glu | Met | |
| | | | 180 | | | | | 185 | | | | | 190 | | | |
| atg | aga | aaa | atc | ttt | gag | cag | gag | caa | gaa | agg | tta | ttt | tat | gaa | ata | 624 |
| Met | Arg | Lys | Ile | Phe | Glu | Gln | Glu | Gln | Glu | Arg | Leu | Phe | Tyr | Glu | Ile | |
| | | | 195 | | | | | 200 | | | | | 205 | | | |
| gaa | ctt | cct | tta | act | cca | gtt | ctt | gct | caa | atg | gag | cat | acc | ggc | att | 672 |
| Glu | Leu | Pro | Leu | Thr | Pro | Val | Leu | Ala | Gln | Met | Glu | His | Thr | Gly | Ile | |
| | 210 | | | | | 215 | | | | | 220 | | | | | |
| cag | gtt | gac | cgg | gaa | gct | tta | aaa | gag | atg | tcg | tta | gag | ctg | gga | gag | 720 |
| Gln | Val | Asp | Arg | Glu | Ala | Leu | Lys | Glu | Met | Ser | Leu | Glu | Leu | Gly | Glu | |
| 225 | | | | | 230 | | | | | 235 | | | | | 240 | |
| caa | att | gaa | gag | tta | atc | cgg | gaa | att | tat | gtg | ctg | gcg | ggg | gaa | gag | 768 |
| Gln | Ile | Glu | Glu | Leu | Ile | Arg | Glu | Ile | Tyr | Val | Leu | Ala | Gly | Glu | Glu | |
| | | | | 245 | | | | | 250 | | | | | 255 | | |
| ttt | aac | tta | aac | tcg | ccc | agg | cag | ctg | gga | gtt | att | ctt | ttt | gaa | aaa | 816 |
| Phe | Asn | Leu | Asn | Ser | Pro | Arg | Gln | Leu | Gly | Val | Ile | Leu | Phe | Glu | Lys | |
| | | | 260 | | | | | 265 | | | | | 270 | | | |
| ctt | ggg | ctg | ccg | gta | att | aaa | aag | acc | aaa | acg | ggc | tac | tct | acc | gat | 864 |
| Leu | Gly | Leu | Pro | Val | Ile | Lys | Lys | Thr | Lys | Thr | Gly | Tyr | Ser | Thr | Asp | |

-continued

```
                275                 280                 285
gcg gag gtt ttg gaa gag ctc ttg cct ttc cac gaa att atc ggc aaa      912
Ala Glu Val Leu Glu Glu Leu Leu Pro Phe His Glu Ile Ile Gly Lys
    290                 295                 300 ata ttg aat tac cgg cag ctt atg aag tta aaa tcc act tat act gac      960
Ile Leu Asn Tyr Arg Gln Leu Met Lys Leu Lys Ser Thr Tyr Thr Asp
305                 310                 315                 320 ggc tta atg cct tta ata aat gag cgt acc ggt aaa ctt cac act act     1008
Gly Leu Met Pro Leu Ile Asn Glu Arg Thr Gly Lys Leu His Thr Thr
                325                 330                 335 ttt aac cag acc ggt act tta acc gga cgc ctg gcg tct tcg gag ccc     1056
Phe Asn Gln Thr Gly Thr Leu Thr Gly Arg Leu Ala Ser Ser Glu Pro
            340                 345                 350 aat ctc caa aat att ccc atc cgg ttg gaa ctc ggt cgg aaa tta cgc     1104
Asn Leu Gln Asn Ile Pro Ile Arg Leu Glu Leu Gly Arg Lys Leu Arg
        355                 360                 365 aag atg ttt ata cct tca ccg ggg tat gat tat att gtt tcg gcg gat     1152
Lys Met Phe Ile Pro Ser Pro Gly Tyr Asp Tyr Ile Val Ser Ala Asp
    370                 375                 380 tat tcc cag att gaa tta agg ctt ctt gcc cat ttt tcc gaa gag ccc     1200
Tyr Ser Gln Ile Glu Leu Arg Leu Leu Ala His Phe Ser Glu Glu Pro
385                 390                 395                 400 aag ctt att gaa gct tac caa aaa ggg gag gat att cac cgg aaa acg     1248
Lys Leu Ile Glu Ala Tyr Gln Lys Gly Glu Asp Ile His Arg Lys Thr
                405                 410                 415 gcc tcc gag gtg ttc ggt gta tct ttg gaa gaa gtt act ccc gag atg     1296
Ala Ser Glu Val Phe Gly Val Ser Leu Glu Glu Val Thr Pro Glu Met
            420                 425                 430 cgc gct cat gcc aag tcg gtg aac ttc ggc att gtt tat ggc att agt     1344
Arg Ala His Ala Lys Ser Val Asn Phe Gly Ile Val Tyr Gly Ile Ser
        435                 440                 445 gat ttt ggt tta ggc aga gac tta aag att ccc cgg gag gtt gcc ggt     1392
Asp Phe Gly Leu Gly Arg Asp Leu Lys Ile Pro Arg Glu Val Ala Gly
    450                 455                 460 aag tac att aaa aat tat ttt gcc aac tat ccc aaa gtg cgg gag tat     1440
Lys Tyr Ile Lys Asn Tyr Phe Ala Asn Tyr Pro Lys Val Arg Glu Tyr
465                 470                 475                 480 ctc gat gaa ctt gtc cgt acg gca aga gaa aag gga tat gtg acc act     1488
Leu Asp Glu Leu Val Arg Thr Ala Arg Glu Lys Gly Tyr Val Thr Thr
                485                 490                 495 tta ttt ggg cga aga cgc tat att cct gag cta tct tca aaa aac cgc     1536
Leu Phe Gly Arg Arg Arg Tyr Ile Pro Glu Leu Ser Ser Lys Asn Arg
            500                 505                 510 acg gtt cag ggt ttt ggc gaa agg acg gcc atg aat act ccc ctt cag     1584
Thr Val Gln Gly Phe Gly Glu Arg Thr Ala Met Asn Thr Pro Leu Gln
        515                 520                 525 ggc tcg gct gcc gat att att aag ctt gca atg att aat gta gaa aaa     1632
Gly Ser Ala Ala Asp Ile Ile Lys Leu Ala Met Ile Asn Val Glu Lys
    530                 535                 540 gaa ctt aaa gcc cgt aag ctt aag tcc cgg ctc ctt ctt tcg gtg cac     1680
Glu Leu Lys Ala Arg Lys Leu Lys Ser Arg Leu Leu Leu Ser Val His
545                 550                 555                 560 gat gag tta gtt tta gaa gtg ccg gcg gaa gag ctg gaa gag gta aaa     1728
Asp Glu Leu Val Leu Glu Val Pro Ala Glu Glu Leu Glu Glu Val Lys
                565                 570                 575 gcg ctg gta aaa ggg gtt atg gag tcg gtg gtt gaa ctg aaa gtg cct     1776
Ala Leu Val Lys Gly Val Met Glu Ser Val Val Glu Leu Lys Val Pro
            580                 585                 590 tta atc gct gaa gtt ggt gca ggc aaa aac tgg tat gaa gcg aag taa     1824
Leu Ile Ala Glu Val Gly Ala Gly Lys Asn Trp Tyr Glu Ala Lys
```

-continued

```
Leu Ile Ala Glu Val Gly Ala Gly Lys Asn Trp Tyr Glu Ala Lys
            595                 600                 605

<210> SEQ ID NO 11
<211> LENGTH: 607
<212> TYPE: PRT
<213> ORGANISM: Carboxydothermus hydrogenoformans

<400> SEQUENCE: 11

Met Glu Lys Leu Ala Glu His Glu Asn Leu Ala Lys Ile Ser Lys Gln
  1               5                  10                  15

Leu Ala Thr Ile Leu Arg Glu Ile Pro Leu Glu Ile Ser Leu Glu Asp
                 20                  25                  30

Leu Lys Val Lys Glu Pro Asn Tyr Glu Glu Val Ala Lys Leu Phe Leu
             35                  40                  45

His Leu Glu Phe Lys Ser Phe Leu Lys Glu Ile Glu Pro Lys Ile Lys
         50                  55                  60

Lys Glu Tyr Gln Glu Gly Lys Asp Leu Val Gln Val Glu Thr Val Glu
 65                  70                  75                  80

Thr Glu Gly Gln Ile Ala Val Val Phe Ser Asp Gly Phe Tyr Val Asp
                 85                  90                  95

Asp Gly Glu Lys Thr Lys Phe Tyr Ser Leu Asp Arg Leu Asn Glu Ile
                100                 105                 110

Glu Glu Ile Phe Arg Asn Lys Lys Ile Ile Thr Asp Asp Ala Lys Gly
            115                 120                 125

Ile Tyr His Val Cys Leu Glu Lys Gly Leu Thr Phe Pro Glu Val Cys
        130                 135                 140

Phe Asp Ala Arg Ile Ala Ala Tyr Val Leu Asn Pro Ala Asp Gln Asn
145                 150                 155                 160

Pro Gly Leu Lys Gly Leu Tyr Leu Lys Tyr Asp Leu Pro Val Tyr Glu
                165                 170                 175

Asp Val Ser Leu Asn Ile Arg Gly Leu Phe Tyr Leu Lys Lys Glu Met
            180                 185                 190

Met Arg Lys Ile Phe Glu Gln Glu Gln Glu Arg Leu Phe Tyr Glu Ile
        195                 200                 205

Glu Leu Pro Leu Thr Pro Val Leu Ala Gln Met Glu His Thr Gly Ile
    210                 215                 220

Gln Val Asp Arg Glu Ala Leu Lys Glu Met Ser Leu Glu Leu Gly Glu
225                 230                 235                 240

Gln Ile Glu Glu Leu Ile Arg Glu Ile Tyr Val Leu Ala Gly Glu Glu
                245                 250                 255

Phe Asn Leu Asn Ser Pro Arg Gln Leu Gly Val Ile Leu Phe Glu Lys
            260                 265                 270

Leu Gly Leu Pro Val Ile Lys Lys Thr Lys Thr Gly Tyr Ser Thr Asp
        275                 280                 285

Ala Glu Val Leu Glu Glu Leu Leu Pro Phe His Glu Ile Ile Gly Lys
    290                 295                 300

Ile Leu Asn Tyr Arg Gln Leu Met Lys Leu Lys Ser Thr Tyr Thr Asp
305                 310                 315                 320

Gly Leu Met Pro Leu Ile Asn Glu Arg Thr Gly Lys Leu His Thr Thr
                325                 330                 335

Phe Asn Gln Thr Gly Thr Leu Thr Gly Arg Leu Ala Ser Ser Glu Pro
            340                 345                 350

Asn Leu Gln Asn Ile Pro Ile Arg Leu Glu Leu Gly Arg Lys Leu Arg
        355                 360                 365
```

```
Lys Met Phe Ile Pro Ser Pro Gly Tyr Asp Tyr Ile Val Ser Ala Asp
    370                 375                 380

Tyr Ser Gln Ile Glu Leu Arg Leu Leu Ala His Phe Ser Glu Glu Pro
385                 390                 395                 400

Lys Leu Ile Glu Ala Tyr Gln Lys Gly Glu Asp Ile His Arg Lys Thr
                405                 410                 415

Ala Ser Glu Val Phe Gly Val Ser Leu Glu Glu Val Thr Pro Glu Met
                420                 425                 430

Arg Ala His Ala Lys Ser Val Asn Phe Gly Ile Val Tyr Gly Ile Ser
            435                 440                 445

Asp Phe Gly Leu Gly Arg Asp Leu Lys Ile Pro Arg Glu Val Ala Gly
    450                 455                 460

Lys Tyr Ile Lys Asn Tyr Phe Ala Asn Tyr Pro Lys Val Arg Glu Tyr
465                 470                 475                 480

Leu Asp Glu Leu Val Arg Thr Ala Arg Glu Lys Gly Tyr Val Thr Thr
                485                 490                 495

Leu Phe Gly Arg Arg Arg Tyr Ile Pro Glu Leu Ser Ser Lys Asn Arg
                500                 505                 510

Thr Val Gln Gly Phe Gly Glu Arg Thr Ala Met Asn Thr Pro Leu Gln
            515                 520                 525

Gly Ser Ala Ala Asp Ile Ile Lys Leu Ala Met Ile Asn Val Glu Lys
    530                 535                 540

Glu Leu Lys Ala Arg Lys Leu Lys Ser Arg Leu Leu Leu Ser Val His
545                 550                 555                 560

Asp Glu Leu Val Leu Glu Val Pro Ala Glu Glu Leu Glu Glu Val Lys
                565                 570                 575

Ala Leu Val Lys Gly Val Met Glu Ser Val Val Glu Leu Lys Val Pro
                580                 585                 590

Leu Ile Ala Glu Val Gly Ala Gly Lys Asn Trp Tyr Glu Ala Lys
            595                 600                 605

<210> SEQ ID NO 12
<211> LENGTH: 26
<212> TYPE: DNA
<213> ORGANISM: Artificial Sequence
<220> FEATURE:
<223> OTHER INFORMATION: Description of artificial sequence:
      amplification primer

<400> SEQUENCE: 12
agcttgctgt attccctcc atcgtg                                        26
```